United States Patent
Kraft et al.

(10) Patent No.: US 6,620,232 B1
(45) Date of Patent: Sep. 16, 2003

(54) DIMENSION STABLE BINDING AGENT SYSTEMS FOR DENTAL APPLICATION

(75) Inventors: Lars Kraft, Länna (SE); Leif Hermansson, Uppsala (SE)

(73) Assignee: Doxa Aktiebolag, Uppsala (SE)

( * ) Notice: Subject to any disclaimer, the term of this patent is extended or adjusted under 35 U.S.C. 154(b) by 0 days.

(21) Appl. No.: 09/807,339

(22) PCT Filed: Oct. 8, 1999

(86) PCT No.: PCT/SE99/01803

§ 371 (c)(1),
(2), (4) Date: Apr. 12, 2001

(87) PCT Pub. No.: WO00/21489

PCT Pub. Date: Apr. 20, 2000

(30) Foreign Application Priority Data

Oct. 12, 1998 (SE) ................................. 9803502

(51) Int. Cl.⁷ ............................. C09C 1/62; A61C 5/00; A61K 6/00
(52) U.S. Cl. ....................... 106/404; 523/116; 523/219; 433/218; 433/219; 433/226; 433/228.1
(58) Field of Search ................................. 523/115, 116, 523/219; 433/219, 218, 226; 524/430, 431, 494; 106/404

(56) References Cited

U.S. PATENT DOCUMENTS

| | | | |
|---|---|---|---|
| 4,234,344 A | * | 11/1980 | Tinsley et al. |
| 4,689,080 A | | 8/1987 | Kawahara et al. |
| 5,522,717 A | * | 6/1996 | Matsumoto et al. |
| 5,693,137 A | * | 12/1997 | Styron |
| 5,697,785 A | * | 12/1997 | Delahaye ................ 433/212.1 |
| 5,858,083 A | * | 1/1999 | Stav et al. |

FOREIGN PATENT DOCUMENTS

| | | | |
|---|---|---|---|
| EP | 0024056 A2 | 2/1981 | |
| EP | 0115058 A2 | 8/1984 | |
| EP | 0024056 B1 | 11/1985 | |
| EP | 0115058 B1 | 1/1988 | |
| EP | A2559627 | 9/1993 | |
| SE | 381808 | 12/1975 | |
| SE | B80065766 | 5/1982 | |
| SE | B463493 | 12/1990 | |
| SE | 0 559 627 | * 9/1993 | ............ A61K/6/06 |
| SE | C2502987 | 3/1996 | |
| WO | A1-9011066 | 10/1990 | |

OTHER PUBLICATIONS

Fu, Yan et al., "Characteristics of Shrinkage Compensating Expansive Cement Containing a Pre-Hydrated High Alumina Cement-Based Expansive Additive," Cement and Concrete Research, vol. 24 (1990), p. 267–276.

* cited by examiner

Primary Examiner—Tae H. Yoon
(74) Attorney, Agent, or Firm—Birch, Stewart, Kolasch & Birch, LLP

(57) ABSTRACT

Chemically bound ceramic system, the binder phase of which essentially consisting of a cement based system, which material comprises one or more expansion compensating additives adapted to give the material dimension stable long time properties.

12 Claims, No Drawings

DIMENSION STABLE BINDING AGENT SYSTEMS FOR DENTAL APPLICATION

This application is the national phase under 35 U.S.C. §371 of PCT International Application No. PCT/SE99/01803 which has an International filing date of Oct. 8, 1999, which designated the United States of America and was published in Swedish.

TECHNICAL FIELD

The present invention relates to a chemically bound ceramic material, the binder phase of which essentially consisting of a cement based system. The primary use for the material is as a dental filling material.

BACKGROUND OF THE INVENTION

The present invention relates to binding agent systems of the cement system type, especially the system CaO—$Al_2O_3$—($SiO_2$)—$H_2O$. This system is used in the building industry for exceptionally hard and tough environments, i.e. acid environments with a high mechanical stress (R J Mangabhai, Calcium Aluminate Cements, Conference volume, E & F N Spon, London 1990). By applying rupture mechanical methods and advanced powder technique on the system, the generally good properties profile of the base system can be considerably improved. Studies in connection with the invention and previous work (SE patent 463 493 and 502 987) have given results which point at a great potential for the system for strong and acid resistant materials as dental filling materials. No dental filling material existing today fulfills all the requirements as to biocompatibility, aesthetics and function, which may be posed by patients and dental care personnel. The situation for different dental filling materials may be concluded according to the following. Amalgam exhibits a generally good strength, but exhibits flaws when it comes to biocompatibility and aesthetics. Plastic composites exhibit a good workability, but exhibit flaws when it comes to erosion and corrosion and in handling for the personnel (allergy problems arisen). Plastic composites shrink at the hardening, which leads to a risk of formation of gaps and, over a time period, carries attack. Glass ionimers exhibit a good binding to dentine, and enamel, but exhibit flaws when it comes to corrosion and strength. Silicate cement exhibits a good compression strength and aesthetics, but suffers from corrosion and strength problems. Different types of inserts exhibit good mechanical properties, but are work demanding and require gluing.

In the following there is given a description of the requirements which generally should be posed for a new practical dental filling material; A good manageability with easy applicability in cavities, a workability which permits a good ability of modelling, a hardening/solidification which is fast enough for the filling work and functioning directly after the dentist appointment. Furthermore, there is required a high level of strength and corrosion resistance, which exceeds the one for existing filling materials, a good biocompatibility, good aesthetics and a secure handling for the personnel, without additives in the materials which may cause allergies or which are toxic. Also, there is required good long time properties in the form of dimension stability. Especially it is a problem if the material expands over time, which may result in fatal tooth bursts.

It has been previously shown, in Swedish patent 502 987, that a complete hydration (which was believed to lower the risk of dimension changes) in a cement system, may take place if a complete soaking and a thereafter following compaction of the cement system is made by aid of a specially designed stopper. The method does however not prevent dimension changes which take place later on and which are related to phase transitions in hydrates or reactions with the surrounding environment (as for example exhalation air with an increased content of carbon dioxide), or other reactions. These reactions and related dimension changes are more noticeable in cases where a high compaction degree is used in the production of the material. A higher compaction degree is however normally desired, since it generally leads to a better strength.

In Yan et al, Characteristics of shrinkage compensation expansive cement containing pre-hydrated high alumina cement-based expansive additive, Cement and Concrete Research, Vol. 24, p 267–276 (1990), the use of the tendency of calcium aluminates to expand, is described. This article and related work on expansive cements describe the possibilities to get standard cement to expand or shrink less, with the use e.g. calcium aluminates, but does not discuss the problems of long time expansion of highly compacted systems or controlling of the expansion of calcium aluminates to very low levels, which is necessary for the use of these binding agent systems in applications according to the present invention.

Other related work and patents, which however do not discuss the basic ideas of the present invention, are for example SE-B-381 808, EP-A-0 024 056 and EP-A-0 115 058, DE 5 624 489 and U.S. Pat. No. 4,689,080.

DESCRIPTION OF THE INVENTION

It is an object of the present invention to provide a material of the type described in the introduction, which material exhibits dimension stable long time properties. The material should also, for dental applications, fulfill the requirements which according to the above are posed for such materials.

This is accomplished according to the invention by the material comprising one or more expansion compensating additives adapted to give the material dimension stable long time properties.

Chemical properties are, besides good mechanical properties, important for dental applications. In one important aspect of the invention, calcium aluminates, i.e. double oxides of CaO (calcium oxide) and Al2O3 (aluminium oxide)—here and below denoted the CA system, which react with water under formation of calcium aluminate hydrates, are used as the main binder phase. This hydration reaction constitutes the setting and hardening process itself To the calcium aluminate cements there are conventionally added some type of aggregates (filler particles), essentially for economic reasons. According to the invention, the choice of the CA cement system, combined with some other cement system or a phase which interacts with the aluminate cements, or combined with an addition of porous aggregates or soft particles, enables a dimension change which is below about 0.20% linearly, often below 0.10%. In special cases, the dimension change may be close to zero expansion.

According to a first embodiment of the invention, the CA system may be used as the sole main binder phase, or with an addition of another cement binder phase in contents decreasing 30 vol-%. Advantageously, there is used additions of ordinary Portland cement (OPC cement) or fine grain silica. While calcium aluminate cements have a tendency to expand seriously at more dense compaction, the combination of CA cement and other phases of the above mentioned type, with the tendency to shrink, may give decreased dimension changes. The CA cements should, in dental applications, be the main phase in the binder phase, since the CA phase contributes to a good strength and acid resistance.

It has become clear that the theories relating to causes for dimension changes, which theories were put forward in connection with SE patent 502 987, i.e. incomplete hydration, do not seem to fully explain the reasons behind the problems in dimension stability. The background of the present invention is more an apprehension that the dimension changes are connected with hydrate phase transitions. This statement, which should not be seen as limiting for the invention, means that calcium aluminate, when it is beginning do be dissolved at the addition of water, forms a gel which thereafter crystallizes and forms hydrate phases, By subsequent hydration reactions and hydrate transitions, different pure Ca-aluminate hydrates as 10-phase, 8-phase, other less defined hydrate phases or transition phases, and finally 6-phase (katoit) may exist, and in the case of silicon containing additives, Ca—Si-aluminate hydrates. By 10-phase, 8-phase and 6-phase it is hereby meant Ca-aluminate phases with 10, 8 and 6 crystal waters respectively, per formula unit. The phase transition of the hydrates may lead to dimension changes, especially expansion, which has been shown by long time evaluation of cement materials. In connection with the present invention, it has surprisingly been found that at an addition of a silicon containing secondary phase, preferably ordinary so called Portland cement (OPC cement with Ca-silicates as main phases) and/or fine crystalline silica (which constitutes said first, preferred embodiment of the invention), unwanted phase transitions may be essentially avoided or the phase transition sequence may be altered, and as a direct consequence thereof, dimension changes may be minimized, especially long time expansion. It is not yet fully clarified how the complicated hydration reactions take place in detail. By addition of Si containing materials, the hydration reactions are modified, which gives dimension stable materials.

It has surprisingly been found that the just mentioned positive effects in connection with the addition of a secondary phase exhibit an optimum at relatively low amounts added. The smallest expansion has thereby been achieved when said secondary phase is OPC cement and/or fine crystalline silica and/or some other Si containing phase, preferably in a total content of 1–20 vol-% and even more preferred 1–10 vol-% in the material. Most preferably, said secondary phase is OPC cement in a content of 1–5 vol-% and/or fine crystalline silica in a content of 1–5 vol-%. There is also referred to the examples in the present description.

It has also surprisingly been found that conventional hardness contributing filler particles, e.g. in the form of hard $Al_2O_3$ particles, may be entirely avoided in the material, or that their use may be minimized, since it is hydrate transitions that are the primary cause for dimension changes over time, especially long time changes. The expansion compensating additives according to the invention thereby act on the cement phase, without any effect of hardness contributing filler particles possibly being present. The fact that it is possible to avoid or minimise the use of hardness contributing filler particles further depend on remaining non-reacted cement—which previously was considered serious from expansion point of view—only giving a minor contribution to the expansion. In connection with the invention it has become clear that non-reacted cement on the contrary acts positively, as an in situ filler material, which contributes to the desired hardness of the material.

According to another embodiment of the invention, the dimension stability of the considered binding agent systems may be thoroughly controlled and controlled to the desired levels, most often to low levels or no dimension change at all, by addition of aggregates (filler particles) with a given geometry/shape, porosity and/or softness. Below, the situation for the cement system $CaO$—$Al_2O_3$—$(SiO_2)$—$H_2O$, which advantageously may be used as a base material for dental filling materials, is described in more detail, but the invention is generally relating to ceramic binding agent systems where the dimension stability is critical.

By choosing aggregates (filler particles) in binding agent systems according to the present invention with a specific geometry and porosity, the binding conditions between the binder phase and aggregates, as well as the dimension stability, may be positively affected. Porous aggregates and other expansion or shrink compensating additives accordingly contribute to the possibilities to control the dimension changes to a desired level by acting as "expansion vessel".

The function of porous aggregates according to the present invention is accordingly to be able to increase the contact surface with the cement phase and to distribute it on smaller extension areas, while retaining a high given content of filler particles. The expansion which originates from the cement phase is primarily taken care of by the porous filler particle, by giving the cement a possibility to expand inside the same. Porous aggregates may advantageously be inert ceramic materials such as aluminium dioxide, zirconium oxide, titanium oxide or zinc oxide or some other oxide or combination of oxides. The porosity may be an open or a closed porosity or a combination thereof. In the normal case, the porous particle or the aggregate has an open porosity of 20–60%, preferably 30–50%. The size of the aggregates is optimally chosen in adaptation to the rupture toughness of the materials, but most often exhibit a diameter below 20 $\mu$m, preferably 5–15 $\mu$m. In the considered materials, small porous aggregates or particles contribute to finer surfaces (lower $R_a$-values) than do solid particles of the corresponding size. The pore openings in the aggregates are adapted to the penetration capacity of the binders. Beneficially, the pore openings are less than 5 $\mu$m, preferably 0.1–5 $\mu$m and even more preferred 1–3 $\mu$m.

Porous aggregates or particles of the above mentioned oxides are preferably produced by sintering fine grain powder, however not at too high temperatures in order for the aggregates or particles to be maintained porous. Aluminium oxide is for example advantageously sintered at about 1500–1600° C. The sintering process is controlled to a desired diameter, porosity and size of pores. Alternatively, the porous aggregates or particles may be produced by fine grain oxide powder being mixed with a compound, e.g. starch, which is brought to evaporate in order to form pores. The material is freeze granulated by being sprayed and frozen.

In a special case, in order to be able to absorb inner tensions created by dimension changes in the binder phase, aggregates with a very high closed porosity may be used, which aggregates burst at a high inner tension to give an internal expansion room. The content of these highly porous particles is limited to 5 vol-% of the binder phase at a maximum. Highly porous microspheres of glass may thereby be used. The highly porous materials are added to the cement mixer in the end of the mixing operation in order to avoid grinding of them. In another special case, a very soft particle is chosen as an additive, which may absorb tensions by having a coefficient of elasticity which decreases the one for the binder phase. In this case there may be used different soft polymers, e.g. plastic balls, or hydrates. When plastic balls are used, which are very small, these may possibly exhibit holes in the middle, for additional deformability. According to one aspect of the invention it has also become clear that the dimension stability of the material may be increased by the included components being brought to exhibit a high level of fine grains. This is also true for strength aspects. The theory is that too large particles have a tendency to be clamped in the structure, which results in different properties in different directions. According to one aspect of the invention there is therefore used a fine grain, finely distributed mixture of binder raw materials which gives a fine, homogenous micro structure. Small areas of extension for the included phases will decrease the inner mechanical tension between phases, and admit an improved possibility for compensation of the internal expansion which may take place in connection with the alteration of phases, such as a continued reaction with the surroundings or phase transitions. The size which may be permitted depends on what level of strength that is desired, typically however, the grain size should have a distribution over 0.5–10 $\mu$m. The calcium aluminates are brought through grinding to essentially exhibit a grain size of about 2–8 $\mu$m, preferably 3–4 $\mu$m or about 3 $\mu$m, and OPC cement, when such is used, is by grinding brought to essentially exhibit a grain size of about 4–8 $\mu$m, preferably 5–7 $\mu$m or about 6 $\mu$m. Fine grain silica, when such is used, should exhibit an even smaller grain size, preferably in the magnitude of below 100 nm, and even more preferred about 10–50 nm, e.g. about 15 nm, which is a type of silica that for example may be bought as a trade merchandise, having been separated in an electrostatic filter in connection with the production of silicon.

The invention is further described in the following examples of embodiments.

EXAMPLE

A series of tests were performed in order to study the effect of different expansion compensating additives on expansion, especially on long time expansion.

Description of Raw Materials

Calcium aluminates of the phases $CaO.Al_2O_3$ and $CaO.2Al_2O_3$ included in e.g. Ca-aluminate cement (Alcoa and Lafarge alternatively), standard cement (Cementa), fine grain silica (Aldrich) and glass spheres (Sil-cell, Stauss GmbH). $Al_2O_3$ (Sumitomo, AKP 30), $ZrO_2$ (3-mol% $Y_2O_3$) from Toyo Soda. Porous particles, self made by fine grain Al-oxide (Sumitomo, AKP 30) (aggregate diameter ca 15 micrometer).

The Examples a)–h) Below Describe
  a) long time expansion of calcium aluminate in a completely hydrated aluminate without additives, but with hardness contributing filler particles (reference)
  b) effect of fine grain level in the cement raw material
  c) effect of secondary phase, OPC cement
  d) effect of secondary phase, fine grain Si-oxide
  e) effect of porous aggregate on b)
  f) effect of porous aggregate on c)
  g) effect of the combination of OPC and fine grain Si-oxide
  h) effect of the combination of different additives
  i) effect of Si containing secondary phases on a pure cement system without hardness contributing filler particles
  j) effect of hardness contributing filler particles on i)

Calcium aluminates, $CaO.Al_2O_3$ and $CaO.2Al_2O_3$, with a molar ratio of about 1:1 is mixed with filler particles and secondary additives (all given contents in relation to the content of calcium aluminate) according to the below. When "aluminium oxide" is mentioned without the type of particles being specified, conventional hardness contributing filler particles are intended.
  a) addition of 40 vol-% aluminium oxide, grinding time 24 h. The cement was previously ground during 20 h.
  b) addition of 40 vol-% aluminium oxide, grinding time 24 h. The cement was previously ground during 80 h.
  c) addition of 40 vol-% aluminium oxide, grinding time 24 h. The cement was previously ground according to b) above. To the calcium aluminate there is added 15 vol-% OPC (ordinary Portland cement/standard cement).
  d) addition of 40 vol-% aluminium oxide, grinding time 24 h. To previously ground calcium aluminate according to b) above, there is added a secondary phase in the form of 10 vol-% fine grain silica.
  e) addition of 20 vol-% aluminium oxide, grinding time 24 h. The cement was previously ground according to b) above. 20 vol-% porous aluminium oxide aggregates (self made) is added only after a grinding time of 20 h.
  f) addition of 20 vol-% aluminium oxide +20 vol-% aluminium oxide in the form of porous particles (aggregates), grinding time 24 h, the aggregates being added only after 20 h. The cement was previously ground according to b) above, however with an addition of a secondary phase in the form of 15 vol-% OPC.
  g) addition of 40 vol-% aluminium oxide, grinding time 24 h. The cement was previously ground according to b) above. To the calcium aluminate there is added 5 vol-% OPC and 5 vol-% fine grain silica.
  h) addition of 20 vol-% aluminium oxide +20 vol-% aluminium oxide in the form of porous particles (aggregates), grinding time 24 h, the aggregates being added only after 20 h. To the calcium aluminate there is in this case added an secondary phase in the form of 5 vol-% OPC and 5 vol-% fine grain silica and 0.5 vol-% glass spheres.
  i) addition of secondary phases in the form of 5 vol-% OPC and 5 vol-% fine grain silica, grinding time 24 h. The cement was previously ground during 80 h.
  j) addition of secondary phases in the form of 5 vol-% OPC and 5 vol-% fine grain silica and hardness contributing filler particles of 10 vol-% $ZrO_2$, grinding time 24 h. The cement was previously ground during 80 h.

The mixtures are ground in a ball mill with inert milling balls of silicon nitride with a filling degree of 35%. As liquid there is used isopropanol. The materials a)–h) were soaked in water after the solvent having been driven off, and were dewatered and filled with a stopper into a hole with a diameter of 4 mm in a container which permitted measuring of the dimensions in an optical microscope. The material were kept moist at 37° C. between the sample measurements, which were performed continuously during up to 180 days.

The result is shown in the table below.

| Sample | Expansion in % after | | | | |
|---|---|---|---|---|---|
| | 1d | 20d | 80d | 120d | 180d |
| a | 0 | 0.12 | 0.68 | 0.82 | 0.83 |
| b | 0 | 0.22 | 0.41 | 0.48 | 0.48 |
| c | 0 | 0.11 | 0.23 | 0.26 | 0.26 |
| d | 0 | 0.12 | 0.13 | 0.13 | 0.13 |
| e | 0 | 0.15 | 0.18 | 0.21 | 0.21 |
| f–j | all values below 0.10% | | | | |

The marginal of error at the measurements is ±0.02%.

The marginal of error at the measurements is ±0.02%.

From the results it can be concluded that the expansion stagnates after about 100 days. For the materials which are very dimension stable (expansion below 0.10%), no evident point in time when stagnation occurs can be found. Furthermore it is clear that An increased grinding time (b) in itself, in relation to the reference (a), almost halves the long time expansion.

When, in addition to this, there is added a secondary phase in the form of OPC cement at a content of 15 vol-% (c), there is almost achieved an additional halving of the long time expansion in relation to (b).

With a secondary phase in the form of fine grain silica at a content of 10 vol-% (d), the long time expansion is even more decreased.

Also with porous aggregates of aluminium oxide at a content of 20 vol-% (e), there is achieved an improved (decreased) long time expansion in relation to (b).

Extremely low expansions were achieved when porous particles and a secondary phase of OPC cement was used in combination.

Extremely low expansions were achieved when secondary phase of both OPC cement and fine grain silica was used in combination.

Extremely low expansions were achieved when porous particles, a secondary phase of both OPC cement and fine grain silica and glass spheres was used in combination.

Extremely low expansions were achieved in the pure cement system, without any hardness contributing filler particles, when only a low content of a Si-containing additive was used.

An extremely low expansion was achieved in the Ca-aluminate system including low contents (10 vol-%) of hardness contributing filler particles, when only Si-containing additives were used for expansion compensation.

The materials which exhibit an extremely low expansion (<0.10%) have, in addition to the expansion properties, a generally good property profile which corresponds to the corresponding cement system without additive. These materials exhibit a compression strength of about 200 MPa, a hardness of H (Vickers 100 g)=150, and an extremely good resistance to acid.

What is claimed is:

1. A chemically bound ceramic dental filling material comprising a binder phase consisting of a cement based system, of which at least 70 volume-% consists of calcium aluminate cement in which the calcium aluminate has a grain size of 10 μm or less, characterized in that the material comprises one or more expansion compensating additives adapted to give the material long term dimensional stability properties, said additive or additives comprising ordinary Portland cement and/or some other organic Si-containing phase having a grain size of 0.5–10 μm and/or fine silica having a grain size of less than 100 nm, at a content of 1–20 volume-% of the material.

2. The material according to claim 1, characterized in that a dimension change , is 0.20% linear change at the most.

3. The material according to claim 1, characterized in that the material is essentially free from hardness contributing filler particles.

4. The material according to claim 1, characterized in that said one or more expansion compensating additives further comprises one or more additives in the group that consists of porous particles, porous aggregates, and soft particles, which soft particles exhibit a coefficient of elasticity that decreases the coefficient of elasticity of the binder phase.

5. The material according to claim 1, wherein said one or more expansion compensating additives is one or more additives selected from the group consisting of porous particles, porous aggregates, soft particles, and a secondary phase which reacts with the binder phase, provided that said additive at least comprises a secondary phase, said secondary phase preferably consisting of ordinary Portland cement and/or fine crystalline silica and/or some other inorganic Si-containing phase, at a total content of 1–10 vol-%, in the material.

6. The material according to claim 5, characterized in that the expansion compensating additives phase consists of ordinary Portland cement at a content of 1–5 vol-% and/or fine crystalline silica at a content of 1–5 vol-%.

7. The material according to claim 4, characterized in that said additive comprises porous particles or porous aggregates, exhibiting a diameter of 2–30 μm, and an open porosity of 20–60%, and wherein the pore openings in the particles/aggregates are less than 5 μm.

8. The material according to claim 7, characterized in that said porous particles or porous aggregates consist essentially of oxides of Al, Zr, Ti, Si, or Zn.

9. The material according to claim 4, characterized in that said additive consists essentially of porous particles, which porous particles consist essentially of glass microspheres with a high closed porosity, which microspheres exhibit a porosity which exceeds 50%.

10. The material according to claim 9, characterized in that said microspheres are included at contents below 2 vol-% of the material.

11. The material according to claim 1, characterized in that a dimension change is less than 0.10% linear change.

12. The material according to claim 4, characterized in that said additive comprises porous particles or porous aggregates exhibiting a diameter of 5–15 μm.

* * * * *

UNITED STATES PATENT AND TRADEMARK OFFICE
CERTIFICATE OF CORRECTION

PATENT NO. : 6,620,232 B1  Page 1 of 1
DATED : September 16, 2003
INVENTOR(S) : Lars Kraft et al.

It is certified that error appears in the above-identified patent and that said Letters Patent is hereby corrected as shown below:

<u>Column 8,</u>
Line 3, insert -- essentially -- after "phase".
Line 6, change "10" to -- 0.5-10 -- and delete "or less".

Signed and Sealed this

Eighteenth Day of April, 2006

JON W. DUDAS
*Director of the United States Patent and Trademark Office*